(12) United States Patent
Fish et al.

(10) Patent No.: US 9,768,628 B2
(45) Date of Patent: Sep. 19, 2017

(54) BATTERY CHARGER

(71) Applicant: Samsung Electronics Co., Ltd., Suwon-si (KR)

(72) Inventors: Ram Fish, San Jose, CA (US); James Schuessler, San Jose, CA (US); Frank Settemo Nuovo, Los Angeles, CA (US); Sheldon George Phillips, Glendale, CA (US)

(73) Assignee: SAMSUNG ELECTRONICS CO., LTD. (KR)

( * ) Notice: Subject to any disclaimer, the term of this patent is extended or adjusted under 35 U.S.C. 154(b) by 61 days.

(21) Appl. No.: 14/587,546

(22) Filed: Dec. 31, 2014

(65) Prior Publication Data

US 2015/0340891 A1    Nov. 26, 2015

Related U.S. Application Data

(60) Provisional application No. 62/002,042, filed on May 22, 2014, provisional application No. 61/922,662, filed on Dec. 31, 2013.

(51) Int. Cl.
*H02J 7/00* (2006.01)

(52) U.S. Cl.
CPC ........... *H02J 7/0042* (2013.01); *H02J 7/0054* (2013.01); *H02J 7/0068* (2013.01)

(58) Field of Classification Search
CPC ....... Y02E 60/12; H02J 7/0054; H02J 7/1423; H01M 10/44; H01M 10/46
USPC ....................................................... 320/103
See application file for complete search history.

(56) References Cited

U.S. PATENT DOCUMENTS

| | | |
|---|---|---|
| 6,595,929 B2 | 7/2003 | Stivoric et al. |
| 6,619,835 B2 | 9/2003 | Kita |
| 7,127,432 B2 | 10/2006 | Rubin et al. |
| 7,512,985 B1 | 3/2009 | Grabarnik et al. |
| 7,618,260 B2 | 11/2009 | Daniel |
| 7,894,888 B2 | 2/2011 | Chan et al. |
| 8,251,903 B2 | 8/2012 | LeBoeuf |
| 8,504,145 B2 | 8/2013 | Kuroda et al. |
| 8,618,930 B2 | 12/2013 | Papadopoulos |
| 8,647,268 B2 | 2/2014 | Tran |
| 8,965,498 B2 | 2/2015 | Katra et al. |
| 2003/0212336 A1 | 11/2003 | Lee et al. |

(Continued)

FOREIGN PATENT DOCUMENTS

| | | |
|---|---|---|
| CN | 101330869 A | 12/2008 |
| EP | 1965697 A2 | 10/2008 |

(Continued)

OTHER PUBLICATIONS

International Search Report corresponding to International Patent Application No. PCT/IB2014/003245, Jul. 29, 2015.

(Continued)

*Primary Examiner* — Arun Williams
(74) *Attorney, Agent, or Firm* — McAndrews, Held & Malloy, Ltd.

(57) ABSTRACT

A system wearable on a body part of a user. The system includes an electronic device powered by a primary power source, and a circuitry coupled to the electronic device. The system also includes a removable secondary power source configured to charge the primary power source with secondary power when coupled to the circuitry.

29 Claims, 9 Drawing Sheets

(56) References Cited

U.S. PATENT DOCUMENTS

| | | |
|---|---|---|
| 2007/0040449 A1 | 2/2007 | Spurlin et al. |
| 2007/0279852 A1 | 12/2007 | Daniel et al. |
| 2008/0171945 A1 | 7/2008 | Dotter |
| 2008/0294058 A1 | 11/2008 | Shklarski |
| 2009/0018409 A1 | 1/2009 | Banet |
| 2009/0048526 A1 | 2/2009 | Aarts et al. |
| 2009/0163820 A1 | 6/2009 | Eerden |
| 2009/0270743 A1 | 10/2009 | Dugan et al. |
| 2009/0306485 A1 | 12/2009 | Bell |
| 2009/0322513 A1 | 12/2009 | Hwang et al. |
| 2010/0076331 A1 | 3/2010 | Chan et al. |
| 2010/0210956 A1 | 8/2010 | Im |
| 2010/0267361 A1 | 10/2010 | Sullivan |
| 2010/0306854 A1 | 12/2010 | Neergaard |
| 2011/0213255 A1 | 9/2011 | Finburgh |
| 2011/0234160 A1* | 9/2011 | Smith ................. H02J 7/0009 320/110 |
| 2011/0245630 A1 | 10/2011 | St. Pierre |
| 2011/0288382 A1 | 11/2011 | Finburgh |
| 2012/0030165 A1 | 2/2012 | Guirguis |
| 2012/0045303 A1 | 2/2012 | MacDonald |
| 2012/0059233 A1 | 3/2012 | Huber |
| 2012/0065514 A1 | 3/2012 | Naghavi et al. |
| 2012/0071731 A1 | 3/2012 | Gottesman |
| 2012/0203076 A1 | 8/2012 | Fatta et al. |
| 2013/0014706 A1 | 1/2013 | Menkes |
| 2013/0141235 A1 | 6/2013 | Utter, II |
| 2013/0165817 A1 | 6/2013 | Horst |
| 2013/0192050 A1 | 8/2013 | LeMieux |
| 2013/0211204 A1 | 8/2013 | Caduff et al. |
| 2013/0261405 A1 | 10/2013 | Lee et al. |
| 2013/0282679 A1 | 10/2013 | Khin |
| 2013/0317333 A1 | 11/2013 | Yang |
| 2013/0318347 A1 | 11/2013 | Moffat |
| 2013/0324072 A1 | 12/2013 | Hsu |
| 2014/0142403 A1 | 5/2014 | Brumback et al. |
| 2014/0159640 A1* | 6/2014 | Yoshikawa ........... H02J 7/0044 320/103 |
| 2015/0173686 A1* | 6/2015 | Furuta ................. A61B 5/1123 600/301 |

FOREIGN PATENT DOCUMENTS

| | | |
|---|---|---|
| JP | 2009-519737 A | 5/2009 |
| KR | 10-1038432 B1 | 1/2011 |
| KR | 10-2011-0012784 A | 9/2011 |
| KR | 10-2012-0033526 A | 4/2012 |
| KR | 20130024468 A | 3/2013 |
| KR | 10-2013-0111713 A | 11/2013 |
| RU | 2008-129670 A | 1/2010 |
| WO | 90-00366 A1 | 1/1990 |
| WO | 2006-018833 A2 | 2/2006 |
| WO | 2006-018833 A3 | 3/2006 |
| WO | 2007-072239 A2 | 6/2007 |
| WO | 2007-072239 A3 | 10/2007 |
| WO | 2010/120945 A1 | 10/2010 |
| WO | 2011/109716 A2 | 9/2011 |
| WO | 2013/175314 A2 | 11/2013 |

OTHER PUBLICATIONS

Notification of Transmittal of the International Search Report and the Written Opinion of the International Searching Authority, or the Declaration corresponding to International Patent Application No. PCT/IB2014/003245, Jul. 29, 2015.

Written Opinion of the International Searching Authority corresponding to International Patent Application No. PCT/IB2014/003245, Jul. 29, 2015.

Notification of Transmittal of the International Search Report and the Written Opinion of the International Searching Authority, or the Declaration corresponding to International Application No. PCT/IB2015/001559, Jan. 20, 2016.

International Search Report corresponding to International Application No. PCT/IB2015/001559, Jan. 20, 2016.

Written Opinion of the International Searching Authority, or the Declaration corresponding to International Application No. PCT/IB2015/001559, Jan. 20, 2016.

Mare et al., Hide-n-sense: preserving privacy efficiently in wireless mhealth, Mobile Networks and Applications 19.3 (Jun. 2014): 331-344. DOI: http://dx.doi.org/10.1007/s11036-013-0447-x ProQuest document ID: 1540736834 Jun. 1, 2014.

Notification of Transmittal of the International Search Report and the Written Opinion of the International Searching Authority, or the Declaration corresponding to International Application No. PCT/IB2015/001979, Mar. 3, 2016.

International Search Report corresponding to International Application No. PCT/IB2015/001979, Mar. 3, 2016.

Written Opinion of the International Searching Authority, or the Declaration corresponding to International Application No. PCT/IB2015/001979, Mar. 3, 2016.

Communication with extended European Search Report corresponding to European Application No. 14196858.6, Jun. 25, 2015 (11 pages).

Communication with European Examination Report corresponding to European Application No. 14196858.6, Oct. 6, 2016, (5 pages).

"Blocks modular smartwatch: Like Project Ara for your wrist," W.Shanklin, Gizmag, Mar. 6, 2014, http://newatlas.com/blocks-modular-smartwatch/31113.

"A Survey on Wearable Sensor-Based Systems for Health Monitoring and Prognosis," A. Pantelopoulos and N.G. Bourbakis, IEEE Transactions on Systems, Man and Cybernetics, vol. 40, No. 1, Jan. 2010.

"Multisensor Fusion in Smartphones for Lifestyle Monitoring," R.K. Ganti, S. Srinivasan, and A. Gacic, International Conference on Body Sensor Networks, 2010.

"A 5.2mW Self-Configured Wearable Body Sensor Network Controller and a 12uW Wireless Powered Sensor for a continuous Health Monitoring System," J.Yoo, L.Yan, S.Lee, Y.Kim, and H-J Yoo, IEEE Journal of Solid-state Circuits, vol. 45, No. 1, Jan. 2010.

Notification Concerning Transmittal of International Preliminary Report on Patentability with International Preliminary Report on Patentability corresponding to PCT/IB2015/001559, Dec. 8, 2016 and Written Opinion of the International Searching Authority mailed Jan. 20, 2016.

Notification of Transmittal of the International Search Report and Written Opinion of the International Searching Authority Authority, or the Declaration corresponding to International Patent Application No. PCT/IB2014/003257, Jan. 11, 2016.

International Search Report corresponding to International Patent Application No. PCT/IB2014/003257, Jan. 11, 2016.

Written Opinion of the International Searching Authority corresponding to International Patent Application No. PCT/IB2014/003257, Jan. 11, 2016.

Notification of Transmittal of the International Search Report and the Written Opinion of the International Searching Authority, or the Declaration corresponding to International Application No. PCT/IB2015/001997, Mar. 3, 2016.

International Search Report corresponding to International Application No. PCT/IB2015/001997, Mar. 3, 2016.

Written Opinion of the International Searching Authority, or the Declaration corresponding to International Application No. PCT/IB2015/001997, Mar. 3, 2016.

* cited by examiner

BATTERY CHARGER

RELATED APPLICATIONS

The present application claims priority to U.S. Provisional Application No. 62/002,042, filed May 22, 2014, and U.S. Provisional Application No. 61/922,662, filed Dec. 31, 2013, all of which are incorporated herein by reference in their entireties.

BACKGROUND

The invention relates to power distribution, and more particularly, to power distribution from a removable power storage to a device wearable on a body part of an individual.

A number of devices wearable on a wrist are available for monitoring and measuring health information, such as, for example, an electrocardiogram ("ECG"), of an individual. These devices continuously monitor, receive, store, and communicate data indicative the health information. Continuous functioning greatly demands resources from their power sources, thus handicapping these devices from being worn for any extended periods of time.

BRIEF SUMMARY

Certain embodiments of the present invention provide a portable power source for charging an electronic device wearable over a wrist of a user.

In one embodiment, the invention provides a system wearable on a body part of a user. The system includes an electronic device powered by a primary power source. The system also includes a circuitry that is coupled to the electronic device, and a removable secondary power source that charges the primary power source with secondary power when the removable secondary power source has been coupled to the circuitry.

In another embodiment, the invention provides a removable power system for providing secondary power to an electronic device wearable on a body part of a user. The electronic device has an interface and a base module that is powered by an internal power source. The removable power system includes a circuitry that is disposed on the interface, and is coupled to the electronic device. The removable power system also includes a fastener that is disposed on the interface. The removable power system also includes a removable power storage to be attached to the interface and to charge the internal power source with secondary power when the removable power storage is coupled to the circuitry.

In yet another embodiment, the invention provides a method of supplying secondary power to an electrical device wearable on a body part of a user. The method includes determining if a removable secondary power source has been attached, and charging the electrical device with secondary power from the removable secondary power source in response to the removable secondary power source having been attached.

BRIEF DESCRIPTION OF SEVERAL VIEWS OF THE DRAWINGS

The features and utilities described in the foregoing brief summary, as well as the following detailed description of certain embodiments of the present general inventive concept below, will be better understood when read in conjunction with the accompanying drawings of which.

For the purpose of illustrating the general inventive concept of the invention, certain embodiments are shown in the drawings. It should be understood, however, that the present invention is not limited to the arrangements and instrumentality shown in the attached drawings.

DETAILED DESCRIPTION

Reference will now be made in detail to the embodiments of the present general inventive concept, examples of which are illustrated in the accompanying drawings, wherein like reference numerals refer to the like elements throughout. The embodiments are described below in order to explain the present general inventive concept while referring to the figures.

Before any embodiments of the invention are explained in detail, it is to be understood that the invention is not limited in its application to the details of construction and the arrangement of components set forth in the following description or illustrated in the drawings.

Advantages and features of the present invention and methods of accomplishing the same may be understood more readily by reference to the following detailed description and the drawings. The present general inventive concept may, however, be embodied in many different forms of being practiced or of being carried out in various ways and should not be construed as being limited to the embodiments set forth herein. Rather, these embodiments are provided so that this disclosure will be thorough and complete and will fully convey the general inventive concept to those skilled in the art, and the present general inventive concept is defined by the appended claims. In the drawings, the thickness of layers and regions are exaggerated for visual clarity.

Also, the phraseology and terminology used in this document are for the purpose of description and should not be regarded as limiting. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

As should also be apparent to one of ordinary skill in the art, the systems shown in the figures are models of what actual systems might be like. Some of the modules and logical structures described are capable of being implemented in software executed by a microprocessor or a similar device, or of being implemented in hardware using a variety of components including, for example, application specific integrated circuits ("ASICs"). A term like "processor" may include or refer to both hardware and/or software. No specific meaning is implied or should be inferred simply due to the use of capitalization.

Likewise, the term "component" or "module", as used herein, means, but is not limited to, a software or hardware component, such as a field programmable gate array (FPGA) or ASIC, which performs certain tasks. A component or module may advantageously be configured to reside in the addressable storage medium and configured to execute on one or more processors. Thus, a component or module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for the components and components or modules may be combined into fewer components and components or modules or further separated into additional components and components or modules.

Unless defined otherwise, all technical and scientific terms used herein have the same meaning as commonly understood by one of ordinary skill in the art to which this invention belongs. Further, unless defined otherwise, all terms defined in generally used dictionaries should have their ordinary meaning. It is noted that the use of any and all examples, or exemplary terms provided herein is intended merely to better illuminate the general inventive concept and is not a limitation on the scope of the invention unless otherwise specified.

Embodiments of the invention relate to a system for providing a wearable device for monitoring an electrocardiogram (ECG) through a wrist of a user. The present application incorporates herein by reference in its entirety U.S. Provisional Application No. 61/922,662, filed Dec. 31, 2013.

Figure 1:
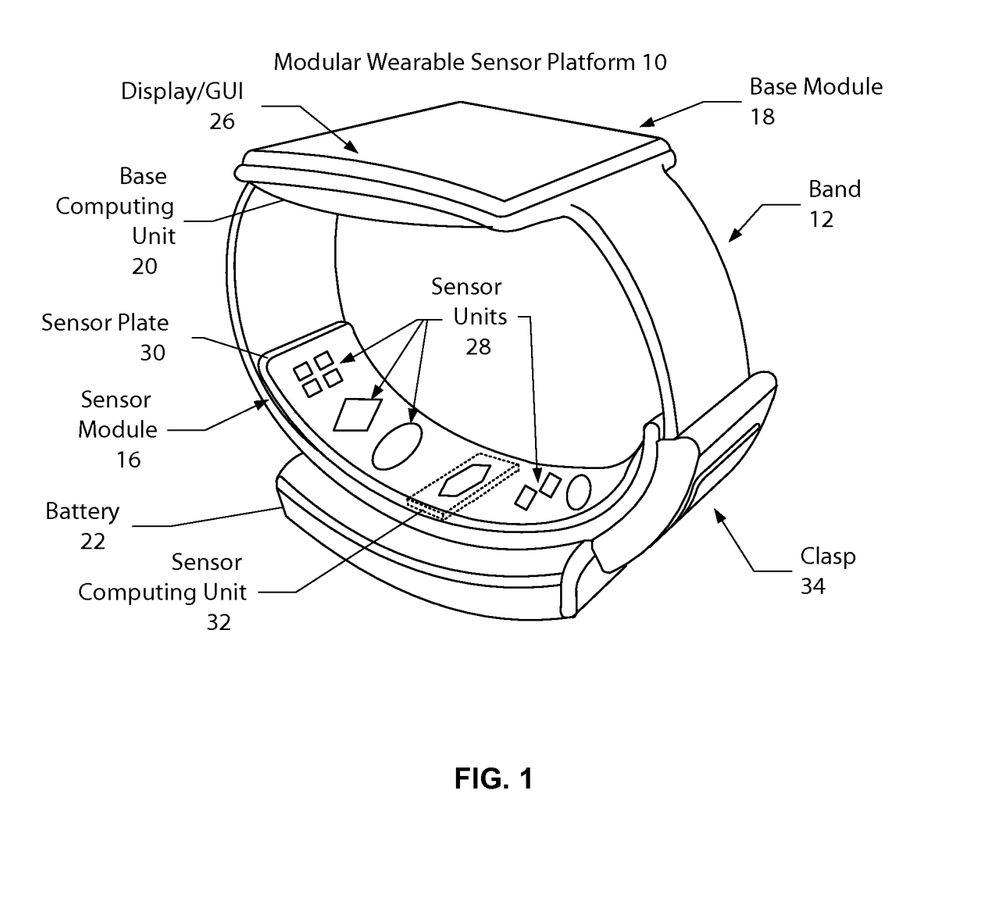
FIG. 1 is a diagram illustrating an embodiment of a modular sensor platform.
Figure 2:
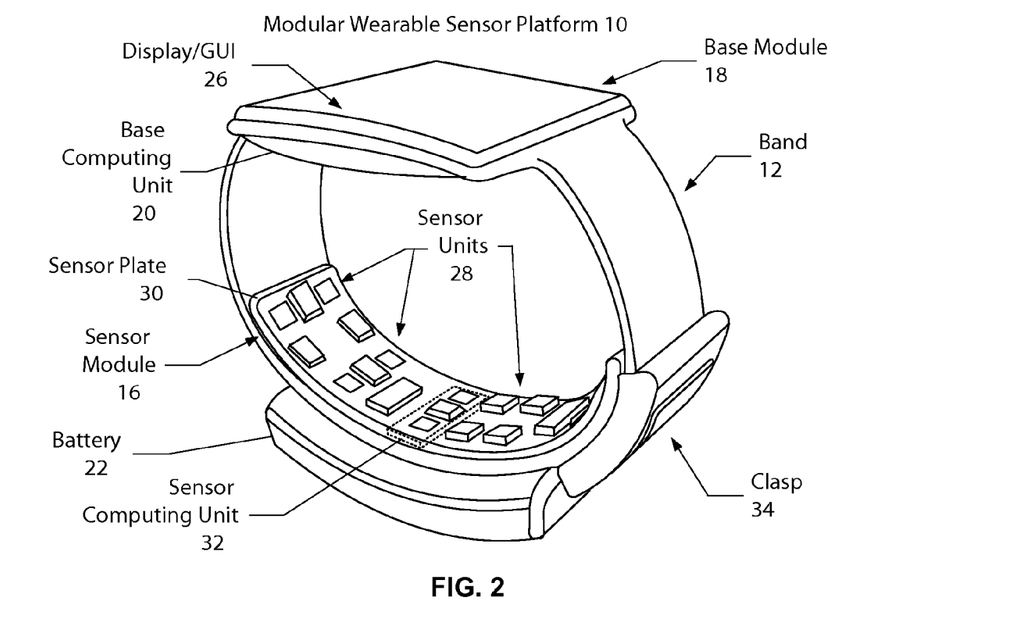
FIG. 2 is an embodiment of the modular sensor platform of FIG. 1.
Figure 3:
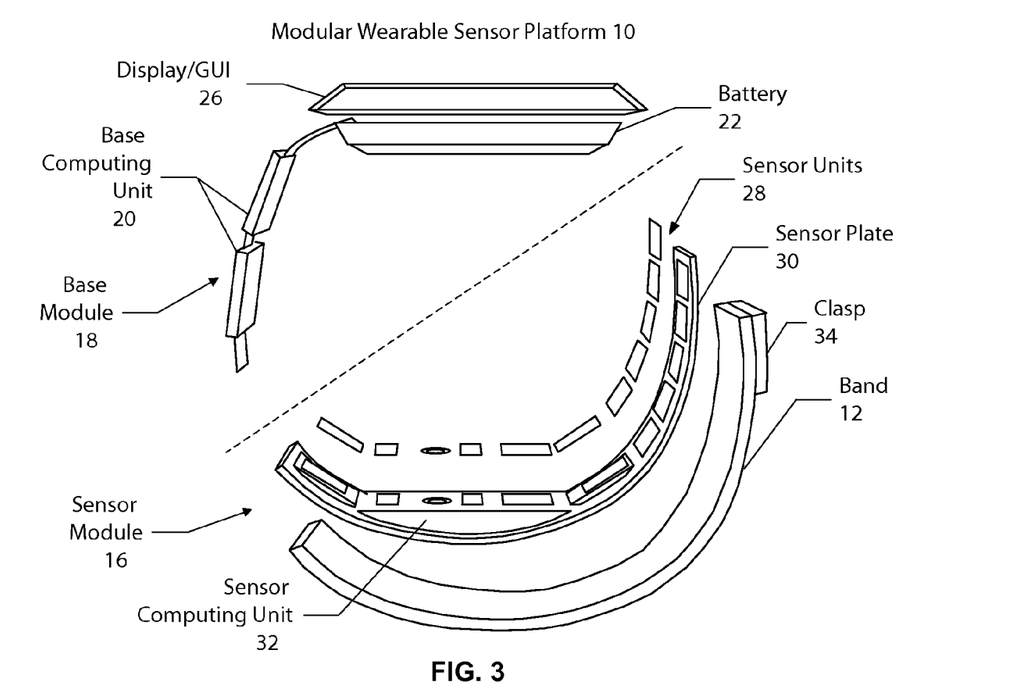
FIG. 3 is a diagram illustrating another embodiment of a modular sensor platform.

FIGS. 1 and 2 are diagrams illustrating embodiments of a modular sensing device or a modular wearable sensor platform 10. FIGS. 1 and 2 depict a perspective view of embodiments of the wearable sensor platform 10, while FIG. 3 depicts an exploded side view of another embodiment of the wearable sensor platform 10. Although the components of the wearable sensor platform in FIGS. 1 and 2 may be substantially the same, the locations of modules and/or components may differ.

In the embodiment shown in FIG. 1, the wearable sensor platform 10 may be implemented as a smart watch or other wearable device that fits on part of a body, here a user's wrist.

The wearable sensor platform 10 may include a base module 18, a band 12, a clasp 34, a battery 22 and a sensor module 16 coupled to the band 12. In some embodiments, the modules and/or components of the wearable sensor platform 10 may be removable by an end user (e.g., a consumer, a patient, a doctor, etc.). However, in other embodiments, the modules and/or components of the wearable sensor platform 10 are integrated into the wearable sensor platform 10 by the manufacturer and may not be intended to be removed by the end user. The wearable sensor platform 10 may be waterproof or water sealed.

The band or strap 12 may be one piece or modular. The band 12 may be made of a fabric. For example, a wide range of twistable and expandable elastic mesh/textiles are contemplated. The band 12 may also be configured as a multi-band or in modular links. The band 12 may include a latch or a clasp mechanism to retain the watch in place in certain implementations. In certain embodiments, the band 12 will contain wiring (not shown) connecting, among other things, the base module 18 and sensor module 16. Wireless communication, alone or in combination with wiring, between base module 18 and sensor module 16 is also contemplated.

The sensor module 16 may be removably attached on the band 12, such that the sensor module 16 is located at the bottom of the wearable sensor platform 10 or, said another way, on the opposite end of the base module 18. Positioning the sensor module 16 in such a way to place it in at least partial contact with the skin on the underside of the user's wrist to allow the sensor units 28 to sense physiological data from the user. The contacting surface(s) of the sensor units 28 may be positioned above, at or below, or some combination such positioning, the surface of the sensor module 16.

The base module 18 attaches to the band 12 such that the base module 18 is positioned at top of the wearable sensor platform 10. Positioning the base module 18 in such a way to place it in at least partial contact with the top side of the wrist.

The base module 18 may include a base computing unit 20 and a display 26 on which a graphical user interface (GUI) may be provided. The base module 18 performs functions including, for example, displaying time, performing calculations and/or displaying data, including sensor data collected from the sensor module 16. In addition to communication with the sensor module 16, the base module 18 may wirelessly communicate with other sensor module(s) (not shown) worn on different body parts of the user to form a body area network, or with other wirelessly accessible devices (not shown), like a smartphone, tablet, display or other computing device. As will be discussed more fully with respect to FIG. 4, the base computing unit 20 may include a processor 36, memory 38, input/output 40, a communication interface 42, a battery 22 and a set of sensors 44, such as an accelerometer/gyroscope 46 and thermometer 48. In other embodiments, the base module 18 can also be other sizes, cases, and/or form factors, such as, for example, oversized, in-line, round, rectangular, square, oval, Carre, Garage, Tonneau, asymmetrical, and the like.

The sensor module 16 collects data (e.g., physiological, activity data, sleep statistics and/or other data), from a user and is in communication with the base module 18. The sensor module 16 includes sensor units 28 housed in a sensor plate 30. For certain implementations, because a portable device, such as a wristwatch, has a very small volume and limited battery power, sensor units 28 of the type disclosed may be particularly suited for implementation of a sensor measurement in a wristwatch. In some embodiments, the sensor module 16 is adjustably attached to the band 12 such that the base module 18 is not fixedly positioned, but can be configured differently depending on the physiological make-up of the wrist.

The sensor units 28 may include an optical sensor array, a thermometer, a galvanic skin response (GSR) sensor array, a bioimpedance (BioZ) sensor array, an electrocardiogram (ECG) sensor, or any combination thereof. The sensor unit 28 may take information about the outside world and supply it to the wearable modular sensor platform 10. The sensors 28 can also function with other components to provide user or environmental input and feedback to a user. For example, a MEMS accelerometer may be used to measure information such as position, motion, tilt, shock, and vibration for use by processor 36. Other sensor(s) may also be employed. The sensor module 16 may also include a sensor computing unit 32. The sensor units 28 may also include biological sensors (e.g., pulse, pulse oximetry, body temperature, blood pressure, body fat, etc.), proximity detector for detecting the proximity of objects, and environmental sensors (e.g., temperature, humidity, ambient light, pressure, altitude, compass, etc.).

In other embodiments, the clasp 34 also provides an ECG electrode. One or more sensor units 28 and the ECG electrode on the clasp 34 can form a complete ECG signal circuit when the clasp 34 is touched. The sensor computing unit 32 may analyze data, perform operations (e.g., calculations) on the data, communicate data and, in some embodiments, may store the data collected by the sensor units 28. In some embodiments, the sensor computing unit 32 receives (for example, data indicative of an ECG signal) from one or more of the sensors of the sensor units 28, and processes the received data to form a predefined representation of a signal (for example, an ECG signal).

The sensor computing unit 32 can also be configured to communicate the data and/or a processed form of the received data to one or more predefined recipients, for example, the base computing unit 20, for further processing, display, communication, and the like. For example, in certain implementations the base computing unit 20 and/or sensor computing unit determine whether data is reliable and determine an indication of confidence in the data to the user.

Because the sensor computing unit 32 may be integrated into the sensor plate 30, it is shown by dashed lines in FIG. 1. In other embodiments, the sensor computing unit 32 may be omitted or located elsewhere on the wearable sensor platform 10 or remotely from the wearable sensor platform 10. In an embodiment where the sensor computing unit 32 may be omitted, the base computing unit 20 may perform functions that would otherwise be performed by the sensor computing unit 32. Through the combination of the sensor module 16 and base module 18, data may be collected, transmitted, stored, analyzed, transmitted and presented to a user.

The wearable sensor platform 10 depicted in FIG. 1 is analogous to the wearable sensor platform 10 depicted in FIGS. 2 and 3. Thus, the wearable sensor platform 10 includes a band 12, a battery 22, a clasp 34, a base module 18 including a display/GUI 26, a base computing unit 20, and a sensor module 16 including sensor units 28, a sensor plate 30, and an optional sensor computing unit 32. However, as can be seen in FIG. 3, the locations of certain modules have been altered. For example, the clasp 34 is closer in FIG. 3 to the display/GUI 26 than clasp 34 is in FIG. 1. Similarly, in FIG. 3, the battery 22 is housed with the base module 18. In the embodiment shown in FIG. 1, the battery 22 is housed on the band 12, opposite to the display 26. However, it should be understood that, in some embodiments, the battery 22 charges the base module 18 and optionally an internal battery (not shown) of the base module 18. In this way, the wearable sensor platform 10 may be worn continuously. Thus, in various embodiments, the locations and/or functions of the modules and other components may be changed.

FIG. 3 is a diagram illustrating one embodiment of a modular wearable sensor platform 10 and components comprising the base module 18. The wearable sensor platform 10 is analogous to the wearable sensor platform 10 in FIGS. 1 and 2 and thus includes analogous components having similar reference labels. In this embodiment, the wearable sensor platform 10 may include a band 12, and a sensor module 16 attached to band 12. The removable sensor module 16 may further include a sensor plate 30 attached to the band 12, and sensor units 28 attached to the sensor plate 30. The sensor module 16 may also include a sensor computing unit 32.

The wearable sensor platform 10 includes a base computing unit 20 in FIG. 3 analogous to the base computing unit 20 and one or more batteries 22 in FIG. 3. For example, permanent and/or removable batteries 22 that are analogous to the battery 22 in FIGS. 1 and 2 may be provided. In one embodiment, the base computing unit 20 may communicate with or control the sensor computing unit 32 through a communication interface 42. In one embodiment, the communication interface 42 may comprise a serial interface. The base computing unit 20 may include a processor 36, a memory 38, input/output (I/O) 40, a display 26, a communication interface 42, sensors 44, and a power management unit 88.

Figure 4:
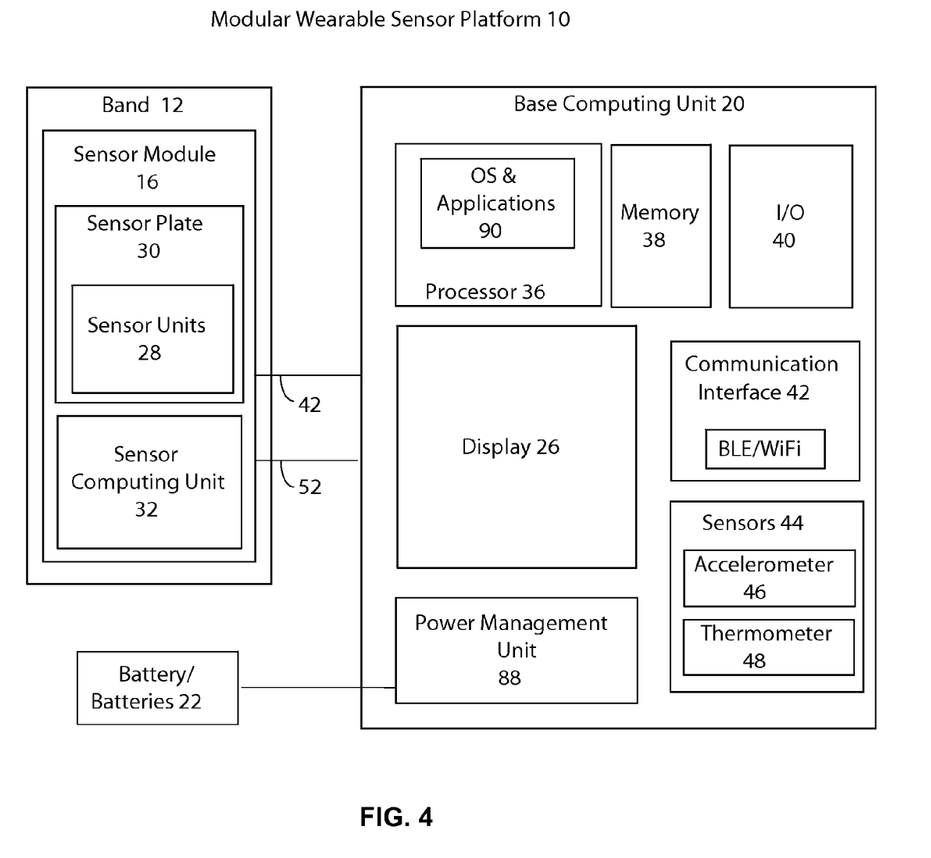
FIG. 4 is a block diagram illustrating one embodiment of the modular sensor platform, including a bandwidth sensor module in connection with components comprising the base computing unit and battery.

The processor 36, the memory 38, the I/O 40, the communication interface 42 and the sensors 44 may be coupled together via a system bus (not shown). The processor 36 may include a single processor having one or more cores, or multiple processors having one or more cores. The processor 36 may be configured with the I/O 40 to accept, receive, transduce and process verbal audio frequency command, given by the user. For example, an audio codec may be used. The processor 36 may execute instructions of an operating system (OS) and various applications. The processor 36 may control on command interactions among device components and communications over an I/O interface. Examples of the OS may include, but not limited to, Linux Android™, Android Wear, and Tizen OS.

The memory 38 may comprise one or more memories comprising different memory types, including RAM (e.g., DRAM and SRAM) ROM, cache, virtual memory microdrive, hard disks, microSD cards, and flash memory, for example. The I/O 40 may comprise a collection of components that input information and output information. Example components comprising the I/O 40 having the ability to accept inputted, outputted or other processed data include a microphone, messaging, camera and speaker. I/O 40 may also include an audio chip (not shown), a display controller (not shown), and a touchscreen controller (not shown). In the embodiment shown in FIG. 4, the memory 38 is external to the processor 36. In other embodiments, the memory 38 can be an internal memory embedded in the processor 36.

The communication interface 42 may include components for supporting one-way or two-way wireless communications and may include a wireless network interface controller (or similar component) for wireless communication over a network in some implementations, a wired interface in other implementations, or multiple interfaces. In one embodiment, the communication interface 42 is for primarily receiving data remotely, including streaming data, which is displayed and updated on the display 26. However, in an alternative embodiment, besides transmitting data, the communication interface 42 could also support voice transmission. In an exemplary embodiment, the communication interface 42 supports low and intermediate power radio frequency (RF) communications. In certain implementations, example types of wireless communication may include Bluetooth Low Energy (BLE), WLAN (wireless local area network), WiMAX, passive radio-frequency identification (RFID), network adapters and modems. However, in another embodiment, example types of wireless communication may include a WAN (Wide Area Network) interface, Wi-Fi, WPAN, multi-hop networks, or a cellular network such as 3G, 4G, 5G or LTE (Long Term Evolution). Other wireless options may include ultra-wide band (UWB) and infrared, for example. The communication interface 42 may also include other types of communications devices (not shown) besides wireless, such as serial communications via contacts and/or USB communications. For example, a micro USB-type USB, flash drive, or other wired connection may be used with the communication interface 42.

In one embodiment, the display 26 may be integrated with the base computing unit 20; while in another embodiment, the display 26 may be external from the base computing unit 20. Display 26 may be flat or curved, e.g., curved to the approximate curvature of the body part on which the wearable sensor module platform 10 is located (e.g., a wrist, an ankle, a head, etc.).

Display 26 may be a touch screen or gesture controlled. The display 26 may be an OLED (Organic Light Emitting Diode) display, TFT LCD (Thin-Film-Transistor Liquid Crystal Display), or other appropriate display technology. The display 26 may be active-matrix. An example display 26 may be an AMOLED display or SLCD. The display may be 3D or flexible. The sensors 44 may include any type of microelectromechanical systems (MEMs) sensor. Such sensors may include an accelerometer/gyroscope 46 and a thermometer 48, for instance.

The power management unit 88 may be coupled to the power source 22 and may comprise a microcontroller that communicates and/or controls power functions of at least the base computing unit 20. Power management unit 88 communicates with the processor 36 and coordinates power management. In some embodiments, the power management unit 88 determines if a power level falls below a certain predefined threshold level or a predefined power threshold. In other embodiments, the power management unit 88 determines if an amount of time or a time threshold has elapsed for secondary charging.

The power source 22 may be a permanent or removable battery, fuel cell or photo voltage cell, etc. The battery 22 may be disposable. In one embodiment, the power source 22 may comprise a rechargeable, lithium ion battery or the like may be used, for example. The power management unit 88 may include a voltage controller and a charging controller for recharging the battery 22. In some implementations, one or more solar cells may be used as a power source 22. The power source 22 may also be powered or charged by AC/DC power supply. The power source 22 may charge by non-contact or contact charging. In one embodiment, the power management unit 88 may also communicate and/or control the supply of battery power to the removable sensor module 16 via power interface 52. In some embodiments, the battery 22 is embedded in the base computing unit 20. In other embodiments, the battery 22 is external to the base computing unit 20.

Other wearable device configurations may also be used. For example, the wearable sensor module platform can be implemented as a leg or arm band, a chest band, a wristwatch, a head band, an article of clothing worn by the user such as a snug fitting shirt, or any other physical device or collection of devices worn by the user that is sufficient to ensure that the sensor units 28 are in contact with approximate positions on the user's skin to obtain accurate and reliable data.

Figure 5:
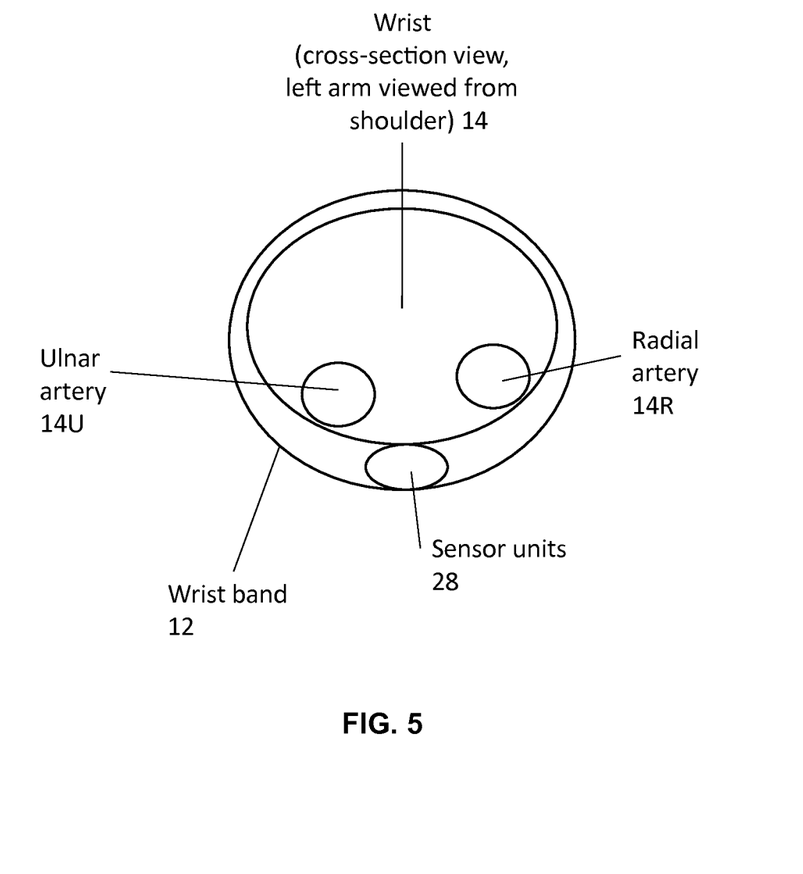
FIG. 5 is a cross-sectional illustration of the wrist with a band mounted sensor in contact for an embodiment used about the wrist.
Figure 6:
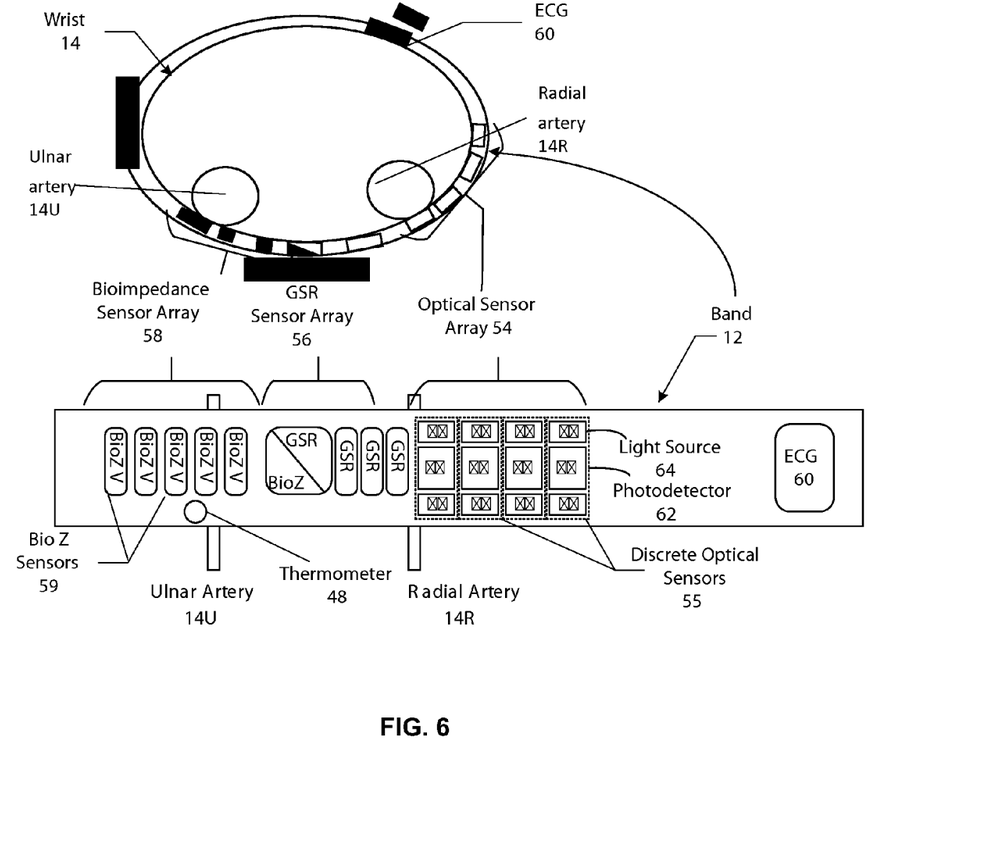
FIG. 6 is a diagram illustrating another embodiment of a modular sensor platform with a self-aligning sensor array system in relation to use about the wrist.

FIG. 5 is a diagram of a cross section of a wrist 14. More specifically, by way of example, FIG. 6 is a diagram illustrating an implementation of a wearable sensor module 10. The top portion of FIG. 6 illustrates the wearable sensor module 10 wrapped around a cross-section of a user's wrist 14, while the bottom portion of FIG. 6 shows the band 12 in an flattened position.

According to this embodiment, the wearable sensor module 10 includes at least an optical sensor array 54, and may also include optional sensors, such as a galvanic skin response (GSR) sensor array 56, a bioimpedance (BioZ) sensor array 58, and an electrocardiogram (ECG) sensor 60, or any combination of which may comprise a sensor array.

According to another embodiment, the sensor units 28 configured as a sensor array(s) comprising an array of discrete sensors that are arranged or laid out on the band 12, such that when the band 12 is worn on a body part, each sensor array may straddle or otherwise address a particular blood vessel (i.e., a vein, artery, or capillary), or an area with higher electrical response irrespective of the blood vessel.

More particularly, as can be seen in FIGS. 5 and 6, the sensor array may be laid out substantially perpendicular to a longitudinal axis of the blood vessel (e.g., radial artery 14R and/or ulnar artery 14U) and overlaps a width of the blood vessel to obtain an optimum signal. In one embodiment, the band 12 may be worn so that the sensor units 28 comprising the sensor array(s) contact the user's skin, but not so tightly that the band 12 is prevented from any movement over the body part, such as the user's wrist 14, or creates discomfort for the user at sensor contact points.

In another embodiment, the sensor units 28 may comprise an optical sensor array 54 that may comprise a photoplethysmograph (PPG) sensor array that may measures relative blood flow, pulse and/or blood oxygen level. In this embodiment, the optical sensor array 54 may be arranged on sensor module 16 so that the optical sensor array 54 is positioned in sufficient proximity to an artery, such as the radial or ulnar artery, to take adequate measurements with sufficient accuracy and reliability.

Further details of the optical sensor array 54 will now be discussed. In general, configuration and layout of each of the discrete optical sensors 55 may vary greatly depending on use cases. In one embodiment, the optical sensor array 54 may include an array of discrete optical sensors 55, where each discrete optical sensor 55 is a combination of at least one photodetector 62 and at least two matching light sources 64 located adjacent to the photodetector 62. In one embodiment, each of the discrete optical sensors 55 may be separated from its neighbor on the band 12 by a predetermined distance of approximately 0.5 to 2 mm.

In one embodiment, the light sources 64 may each comprise a light emitting diode (LED), where LEDs in each of the discrete optical sensors 55 emit light of a different wavelength. Example light colors emitted by the LEDs may include green, red, near infrared, and infrared wavelengths. Each of the photodetectors 62 convert received light energy into an electrical signal. In one embodiment, the signals may comprise reflective photoplethysmograph signals. In another embodiment, the signals may comprise transmittance photoplethysmograph signals. In one embodiment, the photodetectors 62 may comprise phototransistors. In alternative embodiment, the photodetectors 62 may comprise charge-coupled devices (CCD).

Figure 7:
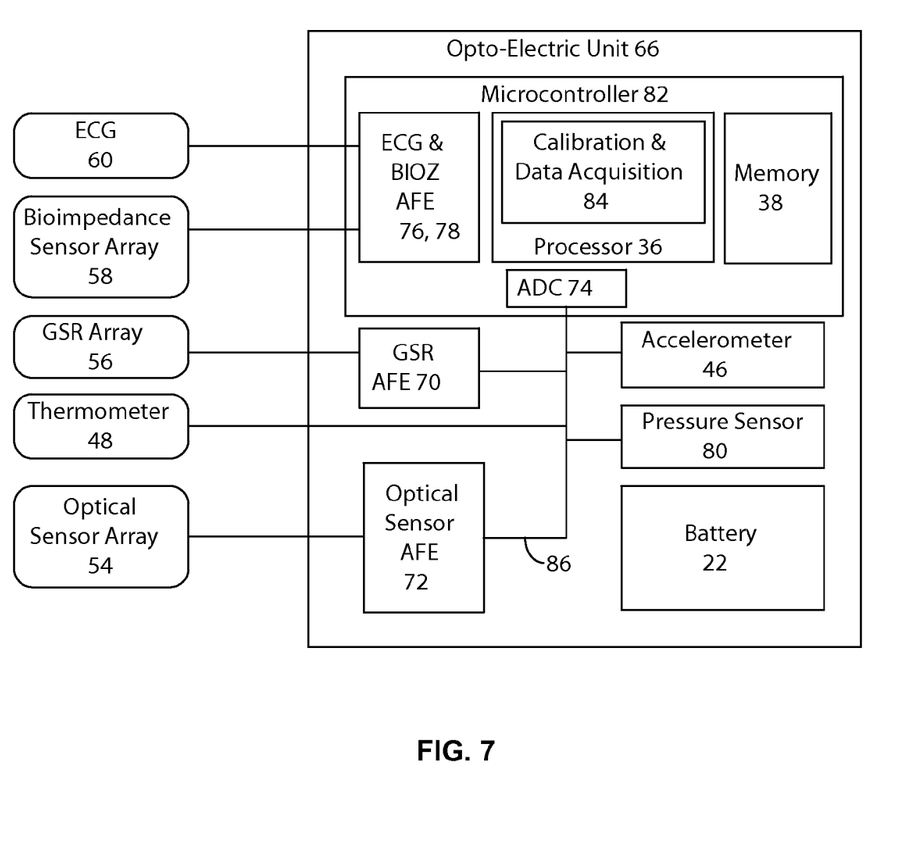
FIG. 7 is a block diagram illustrating components of the modular sensor platform including example sensors and an optical electric unit self-aligning sensor array system in a further embodiment.

FIG. 7 is a block diagram illustrating another configuration for components of wearable sensor module in a further implementation. In this implementation, the ECG 60, the bioimpedance sensor array 58, the GSR array 56, the thermometer 48, and the optical sensor array 54 may be coupled to an optical-electric unit 66 that controls and receives data from the sensors on the band 12. In another implementation, the optical-electric unit 66 may be part of the band 12. In an alternative implementation, the optical-electric unit 66 may be separate from the band 12.

The optical-electric unit 66 may comprise an ECG and bioimpedance (BIOZ) analog front end (AFE) 76, 78, a GSR AFE 70, an optical sensor AFE 72, a processor 36, an analog-to-digital converter (ADC) 74, a memory 38, an accelerometer 46, a pressure sensor 80 and a power source 22.

As used herein, an AFE 68 may comprise an analog signal conditioning circuitry interface between corresponding sensors and the ADC 74 or the processor 36. The ECG and BIOZ AFE 76, 78 exchange signals with the ECG 60 and the bioimpedance sensor array 58. The GSR AFE 70 may exchange signals with the GSR array 56 and the optical sensor AFE 72 may exchange signals with the optical sensor array 54. In one embodiment, the GSR AFE 70, the optical sensor AFE 72, the accelerometer 46, and the pressure sensor 80 may be coupled to the ADC 74 via bus 86. The ADC 74 may convert a physical quantity, such as voltage, to a digital number representing amplitude.

In one embodiment, the ECG and BIOZ AFE 76, 78, memory 38, the processor 36 and the ADC 74 may comprise components of a microcontroller 82. In one embodiment, the GSR AFE 70 and the optical sensor AFE 72 may also be part of the microcontroller 82. The processor 36 in one embodiment may comprise a reduced instruction set computer (RISC), such as a Cortex 32-bit RISC ARM processor core by ARM Holdings, for example. In the embodiment shown in FIG. 7, the memory 38 is an internal memory embedded in the microcontroller 82. In other embodiments, the memory 38 can be external to the microcontroller 82.

According to an exemplary embodiment, the processor 36 may execute a calibration and data acquisition component 84 that may perform sensor calibration and data acquisition functions. In one embodiment, the sensor calibration function may comprise a process for self-aligning one more sensor arrays to a blood vessel. In one embodiment, the sensor calibration may be performed at startup, prior to receiving data from the sensors, or at periodic intervals during operation.

In another embodiment, the sensor units 28 may also comprise a galvanic skin response (GSR) sensor array 56, which may comprise four or more GSR sensors that may measure electrical conductance of the skin that varies with moisture level. Conventionally, two GSR sensors are necessary to measure resistance along the skin surface. According to one aspect of this embodiment, the GSR sensor array 56 is shown including four GSR sensors, where any two of the four may be selected for use. In one embodiment, the GSR sensors 56 may be spaced on the band 2 to 5 mm apart.

In another embodiment, the sensor units 28 may also comprise bioimpedance (BioZ) sensor array 58, which may comprise four or more BioZ sensors 59 that measure bioelectrical impedance or opposition to a flow of electric current through the tissue. Conventionally, only two sets of electrodes are needed to measure bioimpedance, one set for the "I" current and the other set for the "V" voltage. However, according to an exemplary embodiment, a bioimpedance sensor array 58 may be provided that includes at least four to six bioimpedance sensors 59, where any four of electrodes may be selected for "I" current pair and the "V" voltage pair. The selection could be made using a multiplexor. In the embodiment shown, the bioimpedance sensor array 58 is shown straddling an artery, such as the Radial or Ulnar artery. In one embodiment, the BioZ sensors 59 may be spaced on the band 5 to 13 mm apart. In one embodiment, one or more electrodes comprising the BioZ sensors 59 may be multiplexed with one or more of the GSR sensors 56.

In yet another embodiment, the band 12 may include one or more electrocardiogram (ECG) sensors 60 that measure electrical activity of the user's heart over a period of time. In addition, the band 12 may also comprise a thermometer 48 for measuring temperature or a temperature gradient.

According to an exemplary embodiment of an adjustable sensor support structure, a series of sensors supported by flexible bridge structures may be serially connected edge-to-edge along a band. Such a band with bridge supported sensors may be worn, for example, about the wrist 14. When worn about a measurement site such as the wrist 14, the varying topology of the wrist 14 may cause force(s) to simultaneously be exerted upon the bridges due to compliance of the band to the varying topology of the wrist 14.

Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other. Various cloud-based platforms and/or other database platforms may be employed in certain implementations of the modular sensor platform 10 to, for example, receive and send data to the modular sensor platform 10. One such implementation is architecture for multi-modal interactions (not shown). Such architecture can be employed as a layer of artificial intelligence between wearable devices, like modular sensor platform 10, and the larger cloud of other devices, websites, online services, and apps. Such an architecture also may serve to translate (for example by monitoring and comparing) data from the modular sensor platform 10 with archived data, which may be then be used to alert, for example, the user or healthcare professional about changes in condition. This architecture further may facilitate interaction between the modular sensor platform 10 and other information, such as social media, sports, music, movies, email, text messages, hospitals, prescriptions to name a few.

Figures 8, 9:
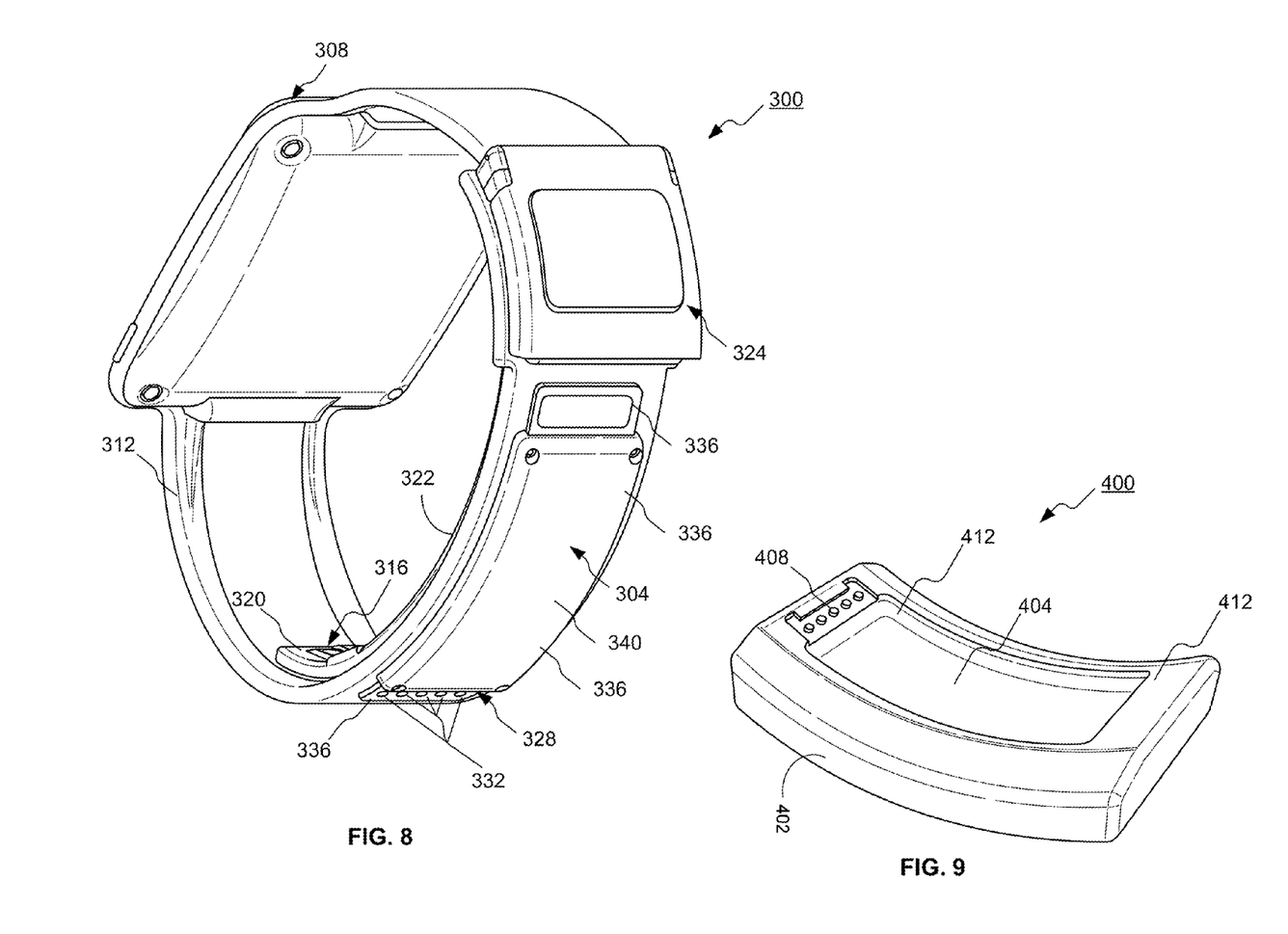
FIG. 8 illustrates another embodiment of a modular wearable sensor platform having a removable power interface.
FIG. 9 illustrates a removable power storage in accordance with embodiments of the present invention.

FIG. 8 illustrates another embodiment of a modular wearable sensor platform or device 300 showing a removable power interface 304. The wearable sensor platform 300 is analogous to the wearable sensor platforms 10 and thus includes analogous components having similar labels. In this embodiment, the wearable sensor platform 300 includes an optional smart device or base module 308, a strap or a band 312, and a sensor module 316 attached to the band 312. In some other embodiments, the wearable sensor platform 300 does not include the optional base module 308. In some embodiments, the base module 308 includes an interface (not shown) similar to the communication interface 210 of FIG. 2. In some embodiments, the modular wearable sensor platform or device 300 is a smart watch or a smart phone.

In the embodiment as shown in FIG. 8, the sensor module 316 is selectively removable, and further includes a sensor plate 320 attached to the band 312, and sensor units (not shown) attached to the sensor plate 320. The sensor module 316 also includes a processor or a sensor computing unit 322 that is similar to the sensor computing unit 32 of FIGS. 2 and 28B of FIG. 1B. The wearable sensor platform 300 also includes a clasp 324 for holding the band 312 over a wrist of a user.

In the embodiment as shown in FIG. 8, the band 312 has various optional fixed sizes to be wearable over different wrist sizes. For example, the band 312 can have different lengths ranging from about 135 mm for a small wrist to about 210 mm for a large wrist. In other embodiments, the band 312 is an adjustable band to be wearable over different wrist sizes. In still other embodiments, the band 312 includes a plurality of sub-bands (not shown) for circulation of air in and around the wrist, thereby provides additional comfort. Further, the band 312 generally consists of chemically inert material, medical-grade material, hypoallergenic silicone, rubber, Graphene, and the like.

In the embodiment as shown in FIG. 8, both the sensor plate 320 and the removable power interface 304 are contoured to conform to a wrist of a user. When the device 300 is worn over the wrist, the sensor plate 320 may be in contact with the skin of the wrist. In other embodiments, the sensor plate 320 is a flexible plate. When selectively pressed, the sensor plate 320 is pressed against the skin of the wrist 14 of FIG. 5, thereby contacting the skin of the wrist 14. In some embodiments, the band 312 has a textured interior surface to minimize slipping.

In the embodiment as shown in FIG. 8, the removable power interface 304 includes a circuitry 328 that is in data communication with the processor 322. In some embodiments, the circuitry 328 is also in data communication with the base module 308, and particularly, an internal or primary power source similar to the battery 22 of FIG. 3 that may be in data communication with and/or that may be embedded in the base module 308, or to the battery 22 of FIG. 3. The circuitry 328, as shown in FIG. 8, includes a plurality of push pins or electrical contacts 332.

In some embodiments, one or more portions of the removable power interface 304, or one or more of the electrical contacts 332 are magnetic in nature, and thus can be used to fasten to any secondary power sources or removable power storage. Further, although five contacts 332 are shown in FIG. 8, it should be understood that other number of contacts 332 can also be used. For example, in some embodiments, the number of contacts 332 is two.

The removable power interface 304 also includes a plurality of fasteners 336 for fastening the secondary power sources or removable power storage to the removable power interface 304, or to the band 312. In some embodiments, the fasteners 336 include one or more of a magnet, a notch, a Velcro, a clip, and the like. In the embodiment as shown in FIG. 8, the fasteners 336 are disposed at either edge of the removable power interface 304. In other embodiments, the fasteners 336 can be embedded with or disposed on a backplate 340 of the removable power interface 304. In yet other embodiments, the fasteners 336 can be disposed on both the backplate 340 and the edges of the removable power interface 304. In the embodiments where the circuitry 328 includes a universal-serial-bus (USB) receptacle, the fasteners 336 can include a clip (not shown) for fastening the secondary power source to the band 312.

Although not shown, it should be understood that the removable power interface 304 can be disposed anywhere on the band 312. For example, the removable power interface 304 can be integrated with the base module 308. In one embodiment, the circuitry 328 is an integral part of the base module 308, and is coupled to an internal or primary power source, similar to the battery 22 of FIG. 3. In such embodiments, a secondary power source may include a universal-serial-bus (USB) interface (not shown), and the circuitry 328 may include a USB receptacle (not shown) for receiving the USB interface. In such embodiments, a secondary power source may include one or more clips for fastening to one or more of the fasteners 336, or to one or more portions of the band 312.

For another example, the removable power interface 304 can have two saddle-like battery modules that fit over the base module 308. In such embodiments, for example, the circuitry 328 can be disposed on both sides of the base module 308. Thus, a secondary power source the two saddle-like battery modules can be fitted over the base module 308 with the saddle-like battery modules seated on either side of the base module 308, and can be coupled to the circuitry 328. In such embodiments, a secondary power source may include one or more clips for fastening to one or more of the fasteners 336, or to one or more portions of the band 312.

Similarly, the removable power interface 304 can be disposed adjacent to one side of the base module 308. In such embodiments, for example, the circuitry 328 can be disposed on the one side of the base module 308. Thus, a secondary power source having a contoured shape can be clipped onto or slid into the band 312 and connected to the base module 308 via the circuitry 328.

It should also be noted that when the circuitry 328 is described, it should be understood that, in some embodiments, there may be internal or external wiring (not shown) electrically coupling one or more portions of the circuitry 328, and one or more of the contacts 332 to the battery 22 of FIG. 3. It should also be understood that, in some embodiments, the circuitry 328 is also coupled to the sensor module 316 with one or more internal and external wiring (not shown). In still other embodiments, the removable power interface 304 can include a sensor module interface (not shown) that can be used to couple to the sensor module 316. The circuitry 328 in such embodiments will thus include internal or external wiring electrically coupling the contacts 332 to the sensor module interface.

FIG. 9 illustrates an embodiment of a portable or secondary power source, or a removable power storage 400 having a removable power storage housing 402. In some embodiments, coupling the removable power storage 400 to the removable power interface 304 results in a modular wearable sensor platform similar to the modular wearable sensor platform 10 of FIG. 1. Although not shown, the removable power storage 400 may house one or more batteries within the housing 402.

The removable power storage 400 as shown in FIG. 9 also includes a receptacle or a bucket 404 for receiving the backplate 340 of FIG. 8, and a plurality of contacts or pogo pins 408 for engaging the electrical contacts 332 of FIG. 8. In some embodiments, the removable power storage 400 also includes fastener portions 412 that fasten the removable power storage 400 to the fasteners 336, as discussed above.

The removable power storage 400 as shown in FIG. 9 has a generally sloping, curved surface to allow for flexing of the wrist 14, to reduce or minimize risk of inadvertent detachment of the removable power storage 400 from the band 312 of FIG. 8. In some embodiments, the removable power storage 400 is a flexible module and coupled to the removable power interface 304 only with one or more of the fasteners 336 as discussed above, thus allowing increased movement of the band 312. Further, when the removable power storage 400 is attached to the modular wearable sensor platform 300, the modular wearable sensor platform 300 can be worn for an extended period of time, for continuous monitoring of different health information, without obstructing any comfort of the user.

Further, although not shown, the removable power storage 400 can also include additional functionalities. For example, in some embodiments, the removable power storage 400 can include an embedded global positioning system (GPS) receiver. Since the GPS receiver is embedded in the removable power storage 400, the GPS receiver can be powered by the secondary power, thus self-powering, and can generate data indicative of a global position of the removable power storage 400.

Figure 10:
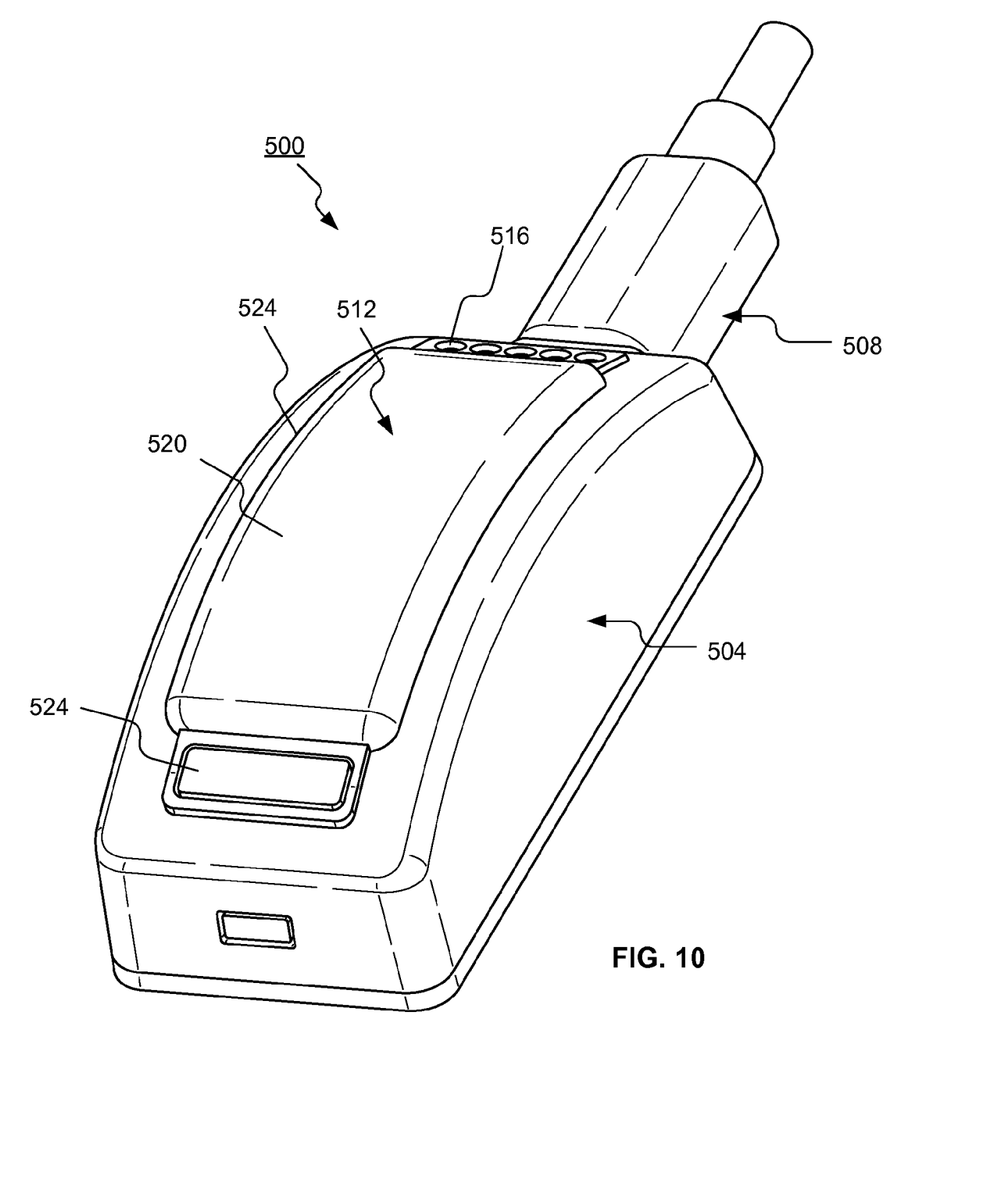
FIG. 10 illustrates a charging station for a removable power storage in accordance with embodiments of the present invention.

FIG. 10 illustrates a charging station 500 for the removable power storage 400 as shown in FIG. 9 in accordance with embodiments of the present invention. The charging station 500 includes a base 504. The base 504 is coupled to a suitable power source, such as, for example, a standard wall plug (not shown) via a power cord 508 to receive power. In the embodiment shown in FIG. 10, the base 504 has a base interface 512 that receives the removable power storage 400 as shown in FIG. 9. In some embodiments, the base interface 512 may generally mirror the removable power interface 304 of FIG. 8. Thus, the base interface 512 also includes a plurality of base contacts 516, and a base backplate 520. In this regard, the base interface 512 also includes one or more fasteners 524 for fastening the removable power storage 400 to the charging station 500. In some other embodiments, the charging station 500 and specifically the base interface 512 may be contoured differently depending on the shape and/or the contour of the removable power storage 400. For example, if the removable power storage 400 has a narrower profile, the base interface 512 will have a corresponding narrower profile. When powered, the charging station 500 charges the removable power storage 400 via the base contacts 516. In some embodiments, the charging station 500 is an intelligent charging station that includes a sensor (not shown) or a processor (not shown) to selectively charge an attached removable power storage. For example, the sensor (not shown) or the processor (not shown) may determine that the attached removable power storage reaches a predefined level of stored power, or has been charged for a predefined amount of time, the sensor (not shown) or the processor (not shown) may terminate charging of the attached removable power storage, until the stored power drops below the predefined level, or after another predefined amount of time has lapsed.

Figure 11:
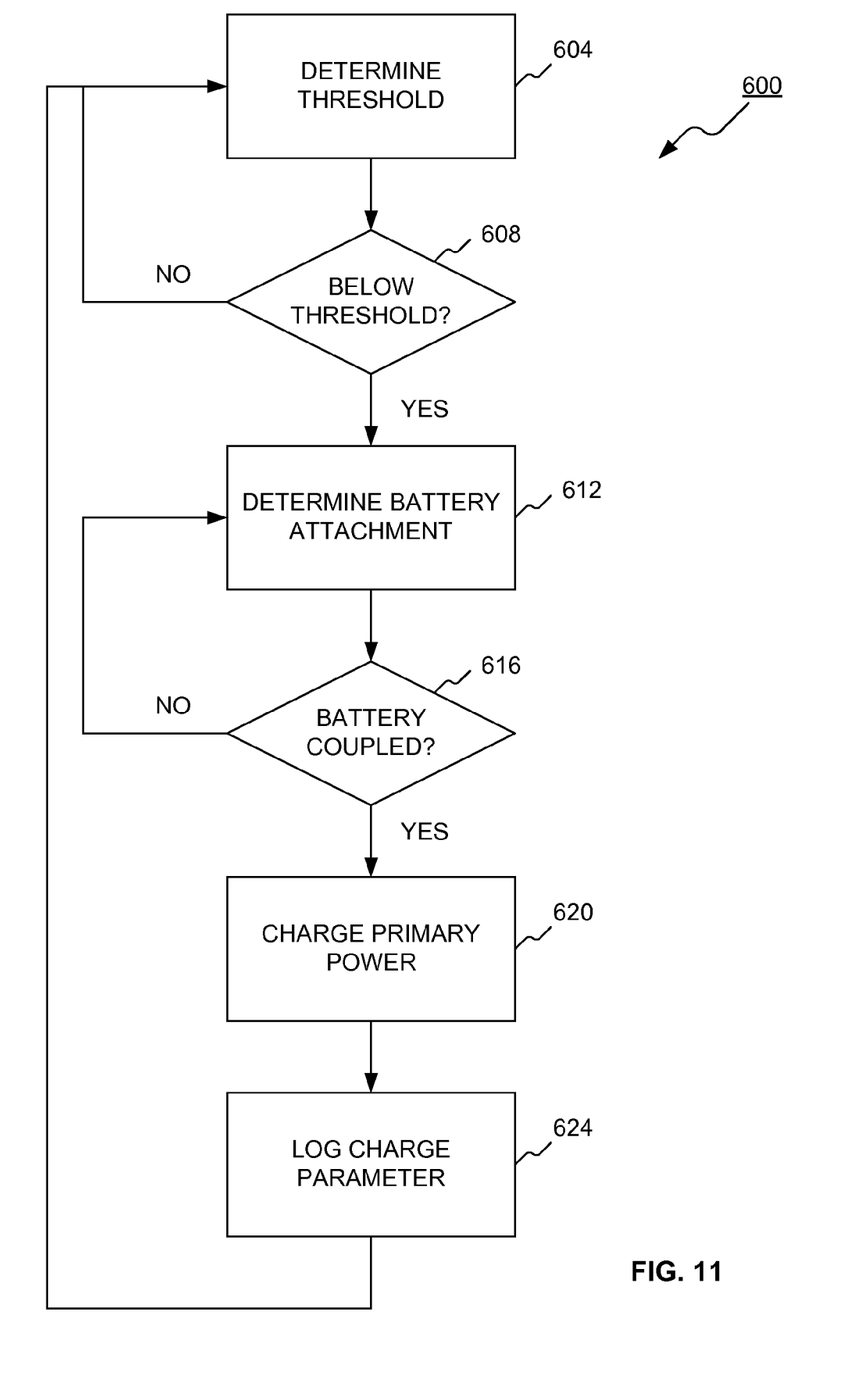
FIG. 11 illustrates an operation flow chart of a modular wearable sensor platform in accordance with embodiments of the present invention.

FIG. 11 illustrates an operation flow chart of a charging process 600 of a modular wearable sensor platform in accordance with embodiments of the present invention. At step 604, the power management unit 88 or the processor 36 obtains a threshold parameter. In some embodiments, the threshold parameter is a time-based parameter. In this regard, the power management unit 88 or the processor 36 of FIG. 4 determines an amount of time elapsed since a last charge. In other embodiments, the threshold parameter is power-based parameter. In this regard, the power management unit 88 or the processor 36 determines a level of power, in amperage, in voltage, or in wattage, of a primary power source similar to the battery 22 of FIG. 3.

At step 608, if it is determined that the threshold has yet to reach a predefined level, for example, a specific amount of time, or a power level, the power management unit 88 or the processor 36 of FIG. 4 continues to obtain the threshold parameter. Otherwise, as determined at step 608 that the threshold has reached a predefined level, for example, a specific amount of time has elapsed, or a power level has fallen below a predefined power threshold, the power management unit 88 or the processor 36 proceeds to an optional step 612.

At step 612, the power management unit 88 or the processor 36 detects if a removable power source similar to the secondary power source 400 of FIG. 9 has been attached, for example, to the removable power interface 304 of FIG. 8. At step 616, if it is determined that the removable power source has not been attached, step 612 is repeated. Otherwise, if it is determined at step 616 that the removable power source has been attached, the primary power source is charged with secondary power from. In some embodiments, the optional step 612 can be eliminated in that the removable power source starts charging the primary power source with secondary power when the removable power source is attached without the determination step.

Step 624 is also an optional step. At step 624, the power management unit 88 or the processor 36 logs parameters of the charging process 600. For example, the power management unit 88 or the processor 36 logs an amount of time elapsed before a power level drops below a predefined power threshold. For another example, the power management unit 88 or the processor 36 logs an amount of power used to charge the internal power source. The power management unit 88 or the processor 36 then can transmit data indicative of the logged entries for further processing.

The present invention has been described in accordance with the embodiments shown, and there could be variations to the embodiments, and any variations would be within the spirit and scope of the present invention. For example, the exemplary embodiment can be implemented using hardware, software, a computer readable medium containing program instructions, or a combination thereof. Software written according to the present invention is to be either stored in some form of computer-readable medium such as a memory, a hard disk, or a CD/DVD-ROM and is to be executed by a processor.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

Additionally, In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

We claim:

1. A system for measuring health information of a user via a body part of the user, the electrical device being wearable on the body part of the user, the system comprising:
   an electronic device powered by an internal primary power source embedded in the electronic device, and configured to measure the health information of the user via the body part;
   a circuitry coupled to the internal primary power source having a predefined threshold, and configured to determine an amount of time elapsed in charging the internal primary power source, and to transmit data; and
   a removable secondary power source configured to charge the internal primary power source with secondary power when the removable secondary power source is coupled to the internal primary power source through the circuitry and in response to the internal primary power source having reached the predefined threshold, and
   wherein the circuitry is further configured to log the amount of time elapsed before a power level of the removable secondary power source drops below the predefined threshold, and to transmit data indicative of the logged amount of time.

2. A system of claim 1, wherein the predefined threshold comprises a time threshold.

3. A system of claim 1, wherein the predefined threshold comprises a power threshold.

4. A system of claim 1, wherein the circuitry includes a plurality of contacts configured to electrically couple the removable secondary power source to the primary power source.

5. A system of claim 1, further comprising a modular sensing device configured to be removably coupled to the electronic device and being powered by the primary power source.

6. A system of claim 1, further comprising a fastener configured to couple the removable secondary power source to the circuitry.

7. A system of claim 6, wherein the fastener comprises one of a magnet, a notch, a Velcro, and a clip.

8. A system of claim 1, wherein the removable secondary power source includes a housing configured to house at least one battery.

9. A system of claim 8, wherein the at least one battery is contoured to the shape of the housing.

10. A system of claim 1, wherein the body part comprises a wrist.

11. A removable power system for providing secondary power to charge an electronic device for measuring health information of a user via a body part of the user, the electrical device being wearable on the body part of the user, the electronic device having an interface and a base module being powered by an internal power source embedded in the electronic device and having a predefined threshold, the removable power system comprising:
   a circuitry coupled to the internal power source of the electronic device that measures the health information of the user via the body part, and configured to determine an amount of time elapsed in charging the internal primary power source, and to transmit data;
   a fastener integrated with the interface; and
   a removable power storage configured to charge the internal power source with secondary power from the removable power storage when the removable power storage is coupled to the internal power source through the circuitry and in response to the removable internal power source having reached the predefined threshold and to the removable power storage having been fastened to the fastener, and
   wherein the circuitry is further configured to log the amount of time elapsed before a power level of the removable secondary power source drops below the predefined threshold, and to transmit data indicative of the logged amount of time.

12. A system of claim 11, wherein the predefined threshold comprises a time threshold.

13. A system of claim 11, wherein the predefined threshold comprises a power threshold.

14. A system of claim 11, wherein the circuitry includes a plurality of contacts configured to electrically couple the removable power storage to the internal power source.

15. A system of claim 11, wherein the fastener comprises one of a magnet, a notch, a Velcro, and a clip.

16. A system of claim 11, further comprising a modular sensing device configured to be removably coupled to the electronic device and being powered by the internal power source.

17. A system of claim 11, wherein the removable power storage includes a housing configured to house at least one battery.

18. A system of claim 17, wherein the at least one battery is contoured to the shape of the housing.

19. A system of claim 11, wherein the body part comprises a wrist.

20. A method of supplying secondary power from a removable secondary power attachable to a wearable electrical device a) being wearable on a body part of a user, and b) being powered by an internal primary power source having a predefined threshold, the method comprising:
   measuring via the wearable electrical device health information of the user via the body part;
   determining via the wearable electrical device if a removable secondary power source has been attached to the wearable electrical device;
   charging the internal primary power source with secondary power from the removable secondary power source in response to the removable secondary power source having been attached and in response to the internal primary power source having reached the predefined threshold;
   logging at wearable electrical device an amount of time elapsed before a power level of the removable secondary power source drops below the predefined threshold, and
   transmitting from wearable electrical device data indicative of the logged amount of time.

21. A method of claim 20, wherein the predefined threshold comprises a time threshold.

22. A method of claim 20, wherein the predefined threshold comprises a power threshold.

23. A method of claim 20, wherein charging the primary power source with the secondary power from the removable secondary power source further comprises charging the primary power source with the secondary power from the removable secondary power source via a plurality of pogo pins of the removable secondary power source.

24. A method of claim 20, further comprising electrically coupling the removable secondary power source to the primary power source with a plurality of contacts of the removable secondary power source.

25. A method of claim 20, further comprising sensing data indicative of electrical activity of a part of the user with a removable modular sensing device being powered by the primary power source.

26. A method of claim 20, further comprising fastening the removable secondary power source to the electrical device with one of a magnet, a notch, a Velcro, and a clip.

27. A method of claim 20, further comprising housing at least one battery in the removable secondary power source in a housing.

28. A method of claim 20, further comprising contouring the at least one battery to the shape of the housing.

29. A method of claim 20, wherein the body part is a wrist.

\* \* \* \* \*